US008814840B2

(12) United States Patent
Evans et al.

(10) Patent No.: US 8,814,840 B2
(45) Date of Patent: Aug. 26, 2014

(54) MEDICAL APPARATUS FOR COLLECTING FLUID

(75) Inventors: John James Henry Evans, Hampshire (GB); Nicholas Cole, Hampshire (GB); Chris Evans, Hampshire (GB)

(73) Assignee: Talley Group Limited, Hampshire (GB)

( * ) Notice: Subject to any disclaimer, the term of this patent is extended or adjusted under 35 U.S.C. 154(b) by 264 days.

(21) Appl. No.: 12/668,877

(22) PCT Filed: Jul. 7, 2008

(86) PCT No.: PCT/GB2008/002322
§ 371 (c)(1),
(2), (4) Date: Jan. 12, 2010

(87) PCT Pub. No.: WO2009/007702
PCT Pub. Date: Jan. 15, 2009

(65) Prior Publication Data
US 2010/0191199 A1  Jul. 29, 2010

(30) Foreign Application Priority Data
Jul. 12, 2007  (GB) ................... 0713608.8

(51) Int. Cl.
*A61M 1/00* (2006.01)
*G01F 3/38* (2006.01)
*G01F 22/00* (2006.01)
*G01F 23/00* (2006.01)

(52) U.S. Cl.
CPC ........... *A61M 1/0049* (2013.01); *A61M 1/0003* (2013.01); *A61M 1/0025* (2014.02); *A61M 1/0031* (2013.01); *A61M 1/0001* (2013.01); *A61M 2205/3331* (2013.01); *A61M 2205/50* (2013.01); *A61M 2205/3379* (2013.01); *A61M 2205/3382* (2013.01); *A61M 2205/3386* (2013.01); *G01F 3/38* (2013.01); *G01F 22/00* (2013.01); *G01F 23/00* (2013.01); *G01F 23/0061* (2013.01)
USPC ........... 604/319; 604/317; 604/318; 604/322; 604/323; 604/324; 604/540; 604/543

(58) Field of Classification Search
CPC ............ A61M 1/0003; A61M 1/0021; A61M 1/0023; A61M 1/0031; A61M 1/0049; A61M 1/0001; A61M 2001/0001; A61M 2001/0023; A61M 2001/0025; A61M 2001/0049; A61M 2205/3331; A61M 2205/50; A61M 2205/3379; A61M 2205/3382; G01F 3/38; G01F 19/00; G01F 22/00; G01F 23/00; G01F 23/0061; G01F 23/0046; G05D 9/02
USPC ........................... 604/31; 702/47, 53, 93, 104
See application file for complete search history.

(56) References Cited

U.S. PATENT DOCUMENTS 3,363,626 A * 1/1968 Bidwell et al. ................ 604/151
3,559,647 A * 2/1971 Bidwell et al. ................ 604/321

(Continued)

FOREIGN PATENT DOCUMENTS

EP          0853950 A1   7/1998
WO    WO 96/05873 A1   2/1996

*Primary Examiner* — Adam Marcetich
(74) *Attorney, Agent, or Firm* — Workman Nydegger (57) ABSTRACT

There is described a medical apparatus, which may comprise a fluid collection vessel and a sensor. The sensor is arranged to sense when the fluid collection vessel is substantially full even when the fluid collection vessel is tilted by up to a predetermined angle from its preferred orientation. The fluid collection vessel may comprise a main chamber and a sensor chamber in fluid communication with one another. The sensor is located in the sensor chamber. The fluid inlet, the main chamber and the sensor chamber are arranged such that fluid entering the fluid collection vessel via the fluid inlet flows into the main chamber even when the fluid collection vessel is tilted by up to the predetermined angle from its preferred orientation, and, once the main chamber is full, any further collected fluid flows from the main chamber into the sensor chamber.

19 Claims, 6 Drawing Sheets

(56) References Cited

U.S. PATENT DOCUMENTS

| | | | |
|---|---|---|---|
| RE29,877 E * | 1/1979 | Kurtz et al. | 604/321 |
| 4,533,353 A * | 8/1985 | Akiyama | 604/321 |
| 4,626,248 A | 12/1986 | Scheller | |
| 5,282,744 A * | 2/1994 | Meyer | 433/92 |
| 5,300,050 A * | 4/1994 | Everett et al. | 604/320 |
| 5,397,299 A * | 3/1995 | Karwoski et al. | 604/6.1 |
| 5,656,027 A * | 8/1997 | Ellingboe | 604/541 |
| 5,807,358 A * | 9/1998 | Herweck et al. | 604/320 |
| 6,263,906 B1 * | 7/2001 | Wilson | 137/428 |
| 6,358,218 B1 * | 3/2002 | Want et al. | 600/573 |
| 6,695,823 B1 * | 2/2004 | Lina et al. | 604/304 |
| 7,553,306 B1 * | 6/2009 | Hunt et al. | 604/543 |
| 2002/0193761 A1 * | 12/2002 | Lord | 604/323 |
| 2003/0028175 A1 | 2/2003 | D'Antonio | |
| 2005/0121081 A1 * | 6/2005 | Corbeil et al. | 137/493.9 |
| 2005/0209585 A1 * | 9/2005 | Nord et al. | 604/540 |
| 2006/0149170 A1 * | 7/2006 | Boynton et al. | 601/6 |
| 2007/0016152 A1 | 1/2007 | Karpowicz et al. | |
| 2007/0129707 A1 * | 6/2007 | Blott et al. | 604/543 |
| 2008/0125697 A1 * | 5/2008 | Gao | 604/35 |

* cited by examiner

MEDICAL APPARATUS FOR COLLECTING FLUID

This application is U.S. National Phase of International Application PCT/GB2008/002322, filed Jul 7, 2008 designating the U.S., and published as WO 2009/007702 on Jan 15, 2009, which claims priority to Great Britain Patent Application No. 0713608.8, filed July 12, 2007.

FIELD OF THE INVENTION

The present invention relates to medical apparatus for collecting fluids such as body fluids.

BACKGROUND OF THE INVENTION

Medical apparatus exist for collecting fluids or liquids such as body fluids from patients. One example is a wound treatment apparatus for collecting exudate from a wound.

Known wound treatment apparatus generally consist of a tube, often referred to as a drain, extending from the site of fluid collection to a fluid collection vessel. One end of the tube is inserted into a gauze or other permeable material which is placed within the wound at the fluid collection site, and a protective dressing sheet overlies the gauze and the wound. The other end of the tube is connected to the fluid collection vessel. An air pump is used to subject the fluid collection vessel to negative pressure (i.e. a vacuum) so that fluid is removed from the collection site due to the negative pressure gradient between the collection site and the vessel. Thus, the fluid is collected in the collection vessel for subsequent disposal. If a collection vessel is over filled, the wound treatment therapy is ineffective. Therefore, it is also known to provide sensors to sense when the collection vessel is full. It is important that such sensors be reliable and not trigger too early.

The present invention seeks to provide an alternative medical apparatus for collecting fluid which provides various advantages over those of the prior art.

SUMMARY OF THE INVENTION

According to a first aspect of the present invention, there is provided a medical apparatus for collecting fluid which has been pumped along a fluid collection conduit from a fluid collection site. The apparatus comprises a fluid collection vessel and a sensor. The fluid collection vessel has a preferred orientation in use and has a fluid inlet for receiving fluid. The sensor is arranged to sense when the fluid collection vessel is substantially full even when the fluid collection vessel is tilted by up to a predetermined angle from its preferred orientation.

Therefore, unlike prior devices, the present invention does not prematurely sense that a fluid collection vessel is full if the vessel tilted. This is very useful since the fluid collection vessel is portable and may often be placed, for example, at an angle on a patient bed.

Preferably, the predetermined angle is at least 30 degrees. More preferably, the predetermined angle is at least 45 degrees. Even more preferably, the predetermined angle is at least 60 degrees.

Optionally, the preferred orientation is a preferred vertical orientation and there is no preferred orientation in any other direction.

In one embodiment, the fluid collection vessel comprises a main chamber and a sensor chamber in fluid communication with one another. The sensor is located in the sensor chamber. The fluid inlet, the main chamber and the sensor chamber are arranged such that fluid entering the fluid collection vessel via the fluid inlet flows into the main chamber even when the fluid collection vessel is tilted by up to the predetermined angle from its preferred orientation, and, once the main chamber is full, any further collected fluid flows from the main chamber into the sensor chamber.

Preferably, the fluid collection vessel comprises one or more baffles to restrict the direct flow of fluid from the fluid inlet towards the sensor.

Advantageously, the fluid inlet is located at or near the top of the fluid collection vessel when the fluid collection vessel is in its preferred orientation. This arrangement prevents the pump having to pump fluid into the fluid collection vessel against the pressure of the already collected fluid (which would occur at some point if the fluid inlet were located lower down in the fluid collection vessel).

Advantageously, the main chamber comprises a fluid outlet into the sensor chamber. The main chamber fluid outlet is located close to the collection vessel fluid inlet and is located outside an imaginary cone which, when the fluid collection vessel is in its preferred orientation, extends downwardly and outwardly from the fluid inlet at the predetermined angle.

In a preferred embodiment, the sensor chamber comprises a substantially U-shaped chamber which is substantially vertically oriented when the fluid collection vessel is in its preferred orientation. One limb of the substantially U-shaped chamber is in fluid communication with the main chamber, and the sensor is disposed in the other limb of the substantially U-shaped chamber. This arrangement ensures that the sensor location is one of the last locations in the fluid collection vessel to be filled with fluid.

Optionally, the fluid collection vessel further comprises a fluid transfer chamber in fluid communication between the main chamber fluid outlet and a fluid inlet of the sensor chamber.

Preferably, the sensor triggers when immersed in fluid. More preferably, the sensor comprises two spaced electrical contacts within the fluid collection vessel arranged such that when the fluid collection vessel is substantially full, the fluid completes an electrical circuit between the two spaced contacts.

Optionally, the fluid collection vessel is disposable.

Advantageously, the fluid collection vessel comprises an air outlet located close to the sensor.

In one embodiment, the medical apparatus further comprises a fluid collection conduit for conveying fluid from the fluid collection site to the fluid inlet of the fluid collection vessel.

Optionally, the medical apparatus further comprises a pump operable to pump fluid along the fluid collection conduit from the fluid collection site to the fluid collection vessel. Advantageously, the sensor is arranged to automatically turn off the pump when the sensor senses that the fluid collection vessel is substantially full.

In a preferred embodiment, the pump is operable to apply negative pressure within the fluid collection vessel so as to pump fluid along the fluid collection conduit from the fluid collection site to the fluid collection vessel. Alternatively, the pump is operable to apply positive pressure at the fluid collection site so as to pump fluid along the fluid collection conduit from the fluid collection site to the fluid collection vessel.

There is also provided a medical apparatus for collecting fluid, comprising a fluid collection vessel, a fluid collection conduit and a connector for connecting the fluid collection conduit to the fluid collection vessel. The fluid collection vessel has a fluid inlet. The fluid connection conduit is for conveying fluid from a fluid collection site to the fluid inlet of the fluid collection vessel. The connector comprises a first connector portion coupled to the fluid collection conduit and a second connector portion coupled to the fluid inlet of the fluid collection vessel. The first and second connector portions are moveable from a mutually connected configuration to a mutually disconnected configuration. In the connected configuration, the fluid collection conduit is in fluid communication with the fluid collection vessel. In the disconnected configuration, the first connector portion blocks the flow of fluid out of the fluid collection conduit.

Advantageously, the first connector portion comprises a connector conduit, a barrier and biasing means. The connector conduit is for conveying fluid from the fluid collection conduit to the second connector portion when the connector is in the connected configuration. The barrier is moveable within the connector conduit from a blocking configuration in which the barrier blocks the passage of fluid through the connector conduit to an open configuration in which fluid is able to flow freely through the connector conduit. The biasing means biases the barrier towards the blocking configuration. The barrier is moveable from the blocking configuration to the open configuration by connecting the first connector portion to the second connector portion.

Advantageously, the connector conduit comprises a narrow conduit and a wide conduit arranged end to end such that the barrier forms a watertight seal within the narrow conduit in the blocking configuration. The internal cross-section of the wide conduit is larger that the internal cross-section of the narrow conduit. More advantageously, the barrier comprises a disc and the narrow conduit has a circular cross-section with a diameter equal to the diameter of the disc. Optionally, the wide conduit has a circular cross-section with a diameter larger than the diameter of the disc. In a preferred embodiment, there are guiding members in the wide conduit to prevent lateral movement of the barrier when it is within the wide conduit.

Advantageously, the second connector portion comprises an engagement member arranged to engage with the barrier of the first connector portion so as to move the barrier from the blocking configuration to the open configuration when the first and second connector portions are moved from the disconnected configuration to the connected configuration.

Advantageously, the biasing means comprises a spring.

In a preferred embodiment, the connector comprises a bayonet connection.

BRIEF DESCRIPTION OF THE DRAWINGS

Embodiments of the present invention will now be described by way of example with reference to the accompanying drawings in which.

DETAILED DESCRIPTION OF A PREFERRED EMBODIMENT

Figure 1:
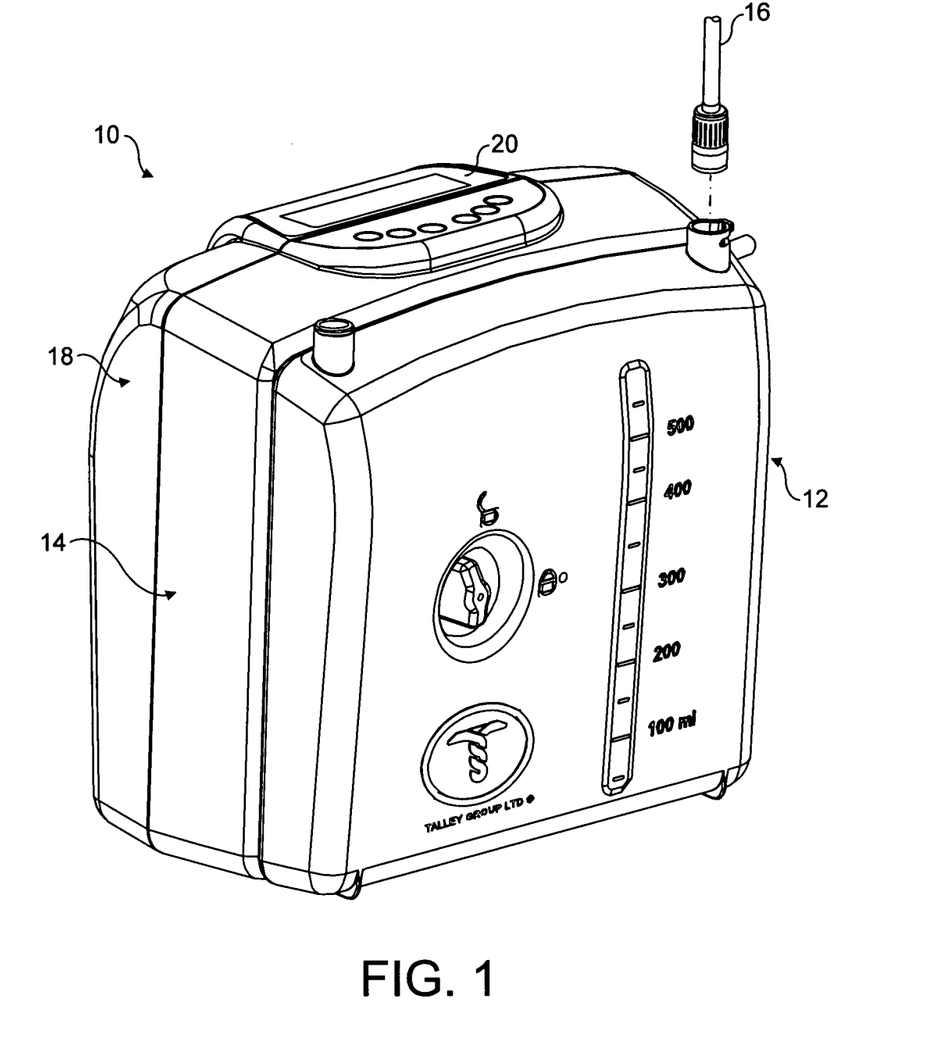
FIG. 1 is a front perspective view of a medical apparatus for collecting fluid according to one embodiment of the present invention.

FIG. 1 shows an embodiment of a medical apparatus 10 for collecting fluid. The medical apparatus 10 is a portable wound treatment apparatus comprising a fluid collection vessel 12, a pump and control assembly 14, a fluid collection conduit in the form of a flexible silicon pipe or tube 16, and a back portion 18. In FIG. 1, the tube 16 is shown disconnected from the fluid collection vessel 12. In use, the tube 16 is connected to the fluid collection vessel 12.

The pump and control assembly 14 comprises a control panel 20 having a number of function buttons and an LCD display. The pump and control assembly 14 is shown in more detail in FIG. 2 which shows a rear view of the medical apparatus 10 with the back portion 18 removed. As shown in the rear view of FIG. 2, the pump and control assembly 14 of the medical apparatus 10 comprises a housing 21 to house a pump 22 having an air inlet 23 and an air outlet 24, pump suspension springs 26, pump impact snubbers 28, a battery module 30, a printed circuit board (PCB) 32, a sensor pin receptacle 34, a DC power connector 36, a communications dataport 38 and an air inlet 40.

Figure 2:
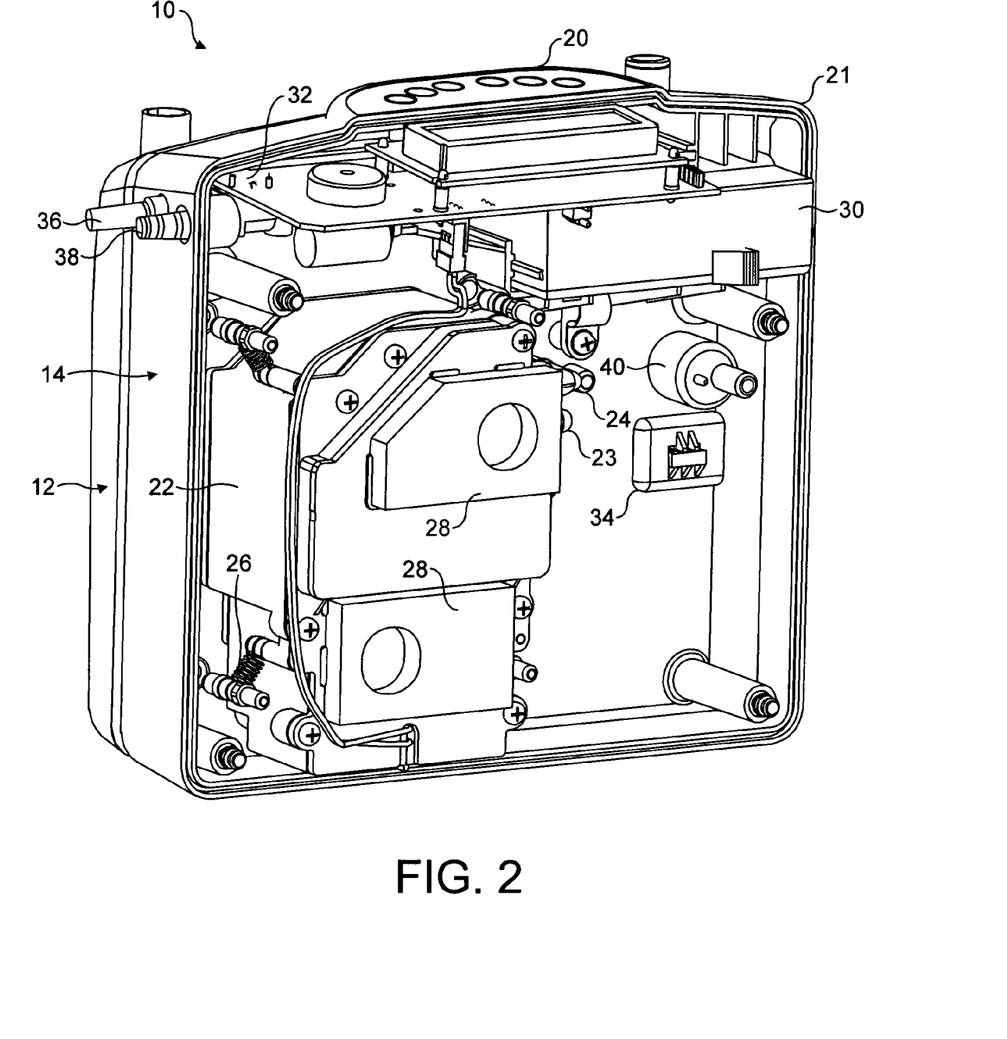
FIG. 2 is a rear perspective view of the medical apparatus shown in FIG. 1 with a back portion removed.

The pump 22 is a 6V DC pneumatic pump with DC power supplied on demand from either the battery 30 or a power source connected to the DC power connector 36. The control PCB 32 routes the DC power to the pump 22. The pump 22 can be used for provision of positive pressure or for provision of vacuum by selection of the appropriate port (i.e. by selection of either air outlet 24 or air inlet 23 respectively). In this embodiment, it is intended that the pump 22 be connected via the air inlet 23 so as to provide vacuum. Thus, the air inlet 23 of the pump is connected to the air inlet 40 of the pump and control assembly 14 via a tube (not shown). In use, the air inlet 40 of the pump and control assembly 14 is connected to an air outlet 66 of the fluid collection vessel 12 so as to enable the pump 22 to subject the fluid collection vessel 12 to a vacuum. The air outlet 66 of the fluid collection vessel is described later with reference to FIG. 4b. Control means exist on the control panel 20 to allow a user to set and regulate the vacuum level.

Figure 3:
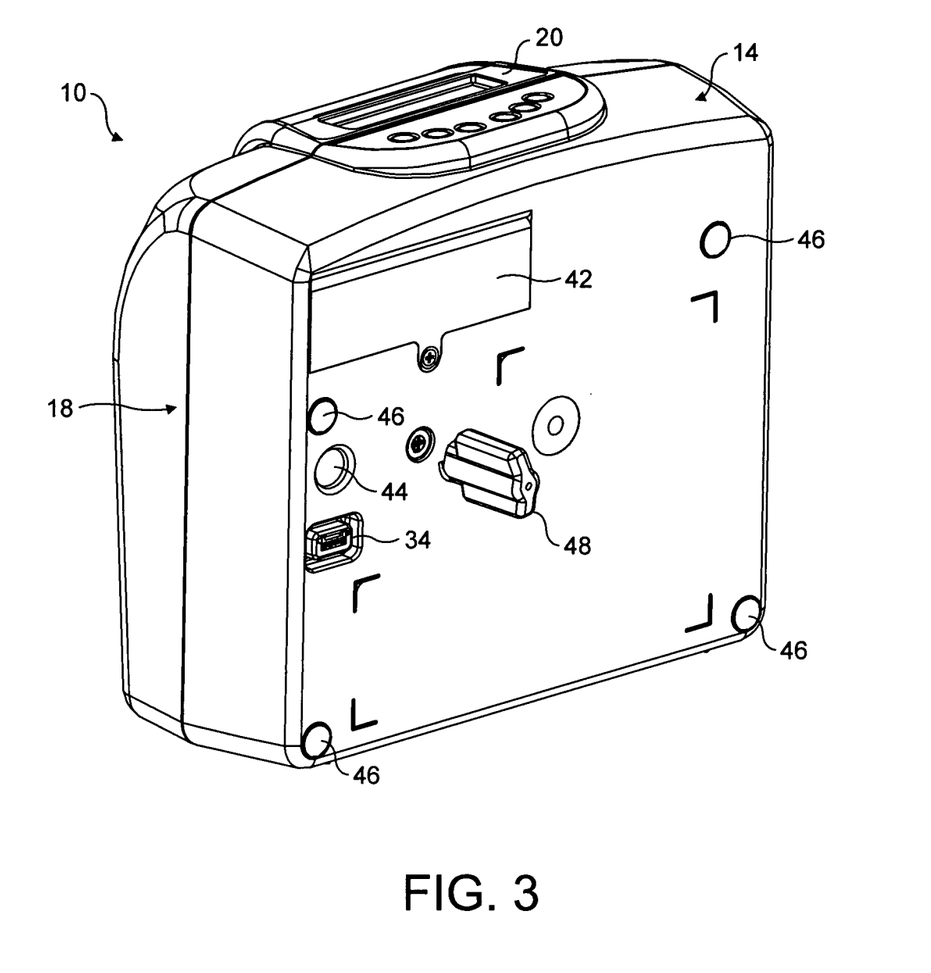
FIG. 3 is a front perspective view of the medical apparatus shown in FIG. 1 with a fluid collection vessel removed.

FIG. 3 shows a front perspective view of the medical apparatus 10 with the fluid collection vessel 12 removed. In the front view shown in FIG. 3, the pump and control assembly 14 can be seen to comprise a cover 42 for the battery module 30, and an aperture 44 forming the front opening of the air inlet 40 for receiving the air outlet of the fluid collection vessel 12. The sensor pin receptacle 34 is also shown. The fluid collection vessel 12 is coupled to the pump and control assembly 14 by means of four sockets 46 and an elongate lock 48.

Figure 4A:
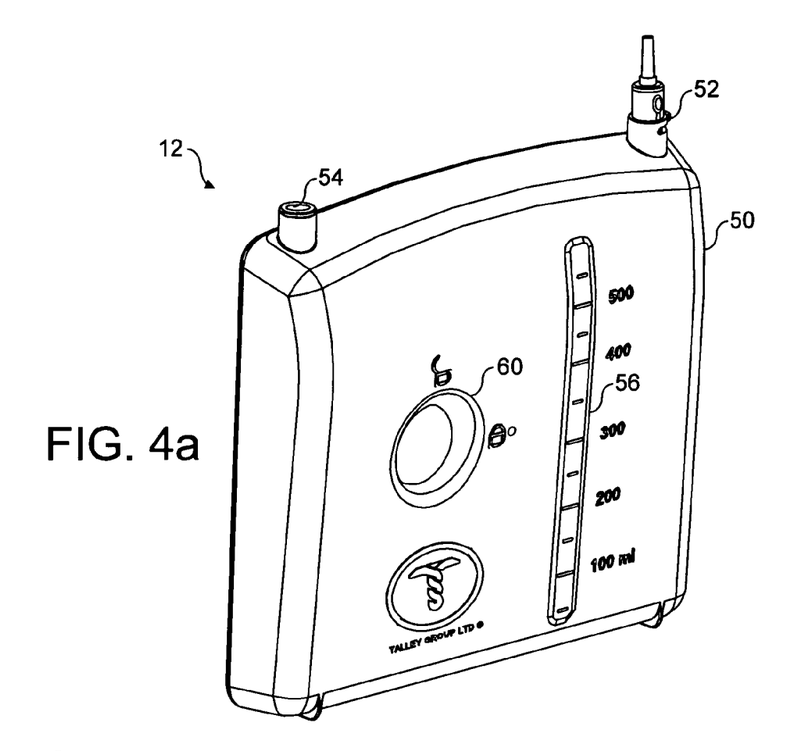
FIGS. 4a and 4b are front and rear perspective views respectively of the fluid collection vessel of the medical apparatus shown in FIG. 1.
Figure 4B:
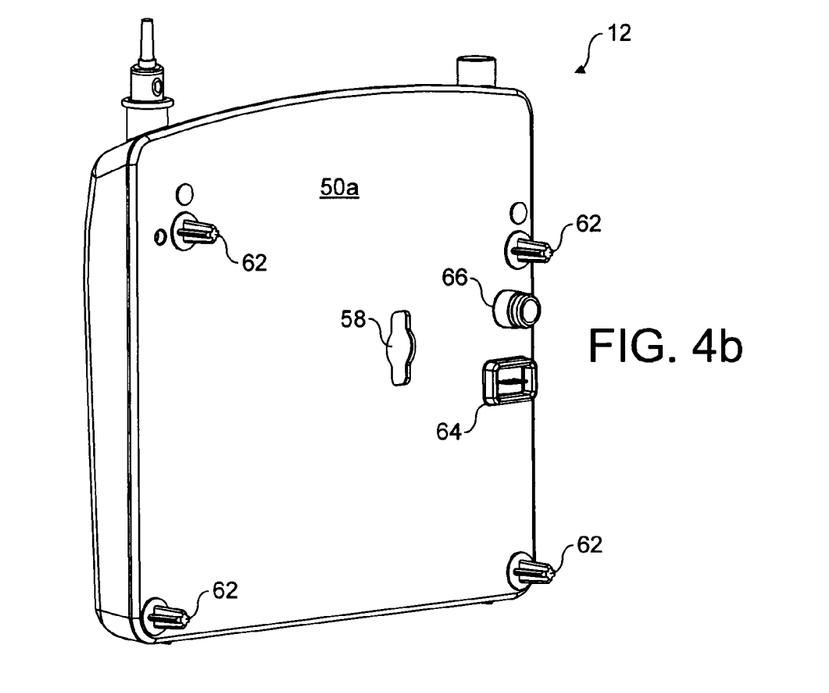

The fluid collection vessel 12 is shown in more detail in the front and rear perspective views of FIGS. 4a and 4b respectively. The fluid collection vessel 12 comprises a housing 50, a fluid inlet 52, a blanking cap 54 for the fluid inlet 52, a window 56, an elongate aperture 58 at the rear of the fluid collection vessel 12 which opens out into a larger cylindrical aperture 60 at the front of the fluid collection vessel 12, four location pegs 62, a sensor 64 and an air outlet 66.

The blanking cap 54 is shown in a stowed position on a blanking cap holder remote from the fluid inlet 52. The blanking cap 54 is operable to cover the fluid inlet 52 when the medical apparatus 10 is not in use. In contrast, when the medical apparatus 10 is in use, the fluid inlet 52 is adapted to be connected to the tube 16 shown in FIG. 1.

The window 56 is a vertical column of at least partially transparent material which provides a fluid level indication when the fluid collection vessel 12 is in use. The window 56 comprises graduation marks for this purpose. The remainder of the housing 50 is not transparent. In one embodiment, the housing 50 and the window 56 are integrally moulded from the same material, with the window 56 being thinner than the thickness of the housing 50 so as to provide partial transparency. Preferably, the window 56 is thin enough to enable sight of the fluid within, but not thin enough to enable the colour of the fluid within to be discerned. Furthermore, in this embodiment, the window has a smooth finish to enable partial transparency, whereas the housing 50 has a textured finish to further obscure the contents. The housing 50 comprises a flat rear half 50a and a profiled front half 50b that are bonded together.

In use, the fluid collection vessel 12 is coupled to the pump and control assembly 14 by inserting the location pegs 62 in the back of the fluid collection vessel 12 into the corresponding sockets 46 in the front of the pump and control assembly 14. At the same time, the elongate lock 48 is inserted into the elongate aperture 58 in the rear of the fluid collection vessel 12 such that the elongate lock 48 is eventually received within the cylindrical aperture 60. The fluid collection vessel 12 is then locked in place by turning the elongate lock 48 by a quarter turn so that it is no longer aligned with the elongate aperture 58 at the rear of the fluid collection vessel 12. The fluid collection vessel may then be disengaged from the pump and control assembly 14 by turning the elongate lock 48 so that it is once again in line with the elongate aperture 58 at the rear of the fluid collection vessel 12.

Figures 5, 6A, 6B:
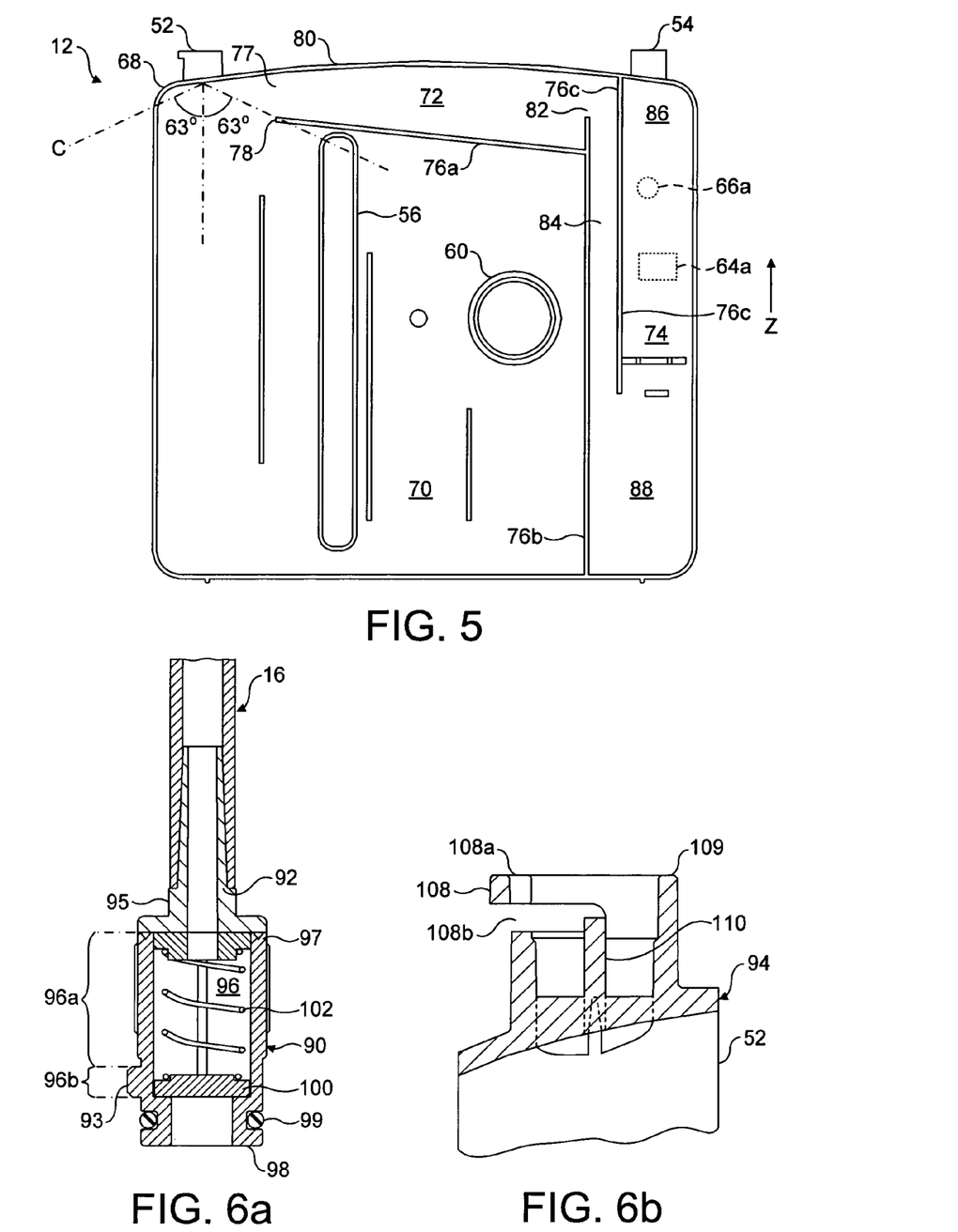
FIG. 5 is a cross-sectional view through the fluid collection vessel shown in FIGS. 4a and 4b.
FIGS. 6a and 6b are cross-sectional views of first and second connector portions for connecting a fluid collection conduit to the fluid collection vessel shown in FIGS. 4a and 4b.

The air outlet 66 is located at the rear of the fluid collection vessel 12. The air outlet 66 is in the form of a parallel male spigot with an O-ring. The air outlet 66 further comprises a tube mount having an internal diameter of 6 mm. In normal operation, fluid that has been collected in the fluid collection vessel 12 should not come into contact with the air outlet (see below). Nonetheless, the air outlet 66 is gated with a hydrophobic membrane/filter so as to enable retention of fluid within the fluid collection vessel 12 in the rare circumstances when collected fluid comes into contact with the air outlet 66. The air outlet 66 is further gated with an antibacterial filter for the purpose of odour prevention. In one embodiment, the antibacterial filter is a carbon membrane (i.e. a carbon bacterial filter) for bacterial protection. However, in a. preferred embodiment, the antibacterial filter is more substantial than a thin membrane and instead takes the form of a three-dimensional block of granular antibacterial media, including carbon and/or other antibacterial substances. The antibacterial filter may in itself be disposable, or may be integral with the disposable fluid collection vessel 12. In FIGS. 4b and 5, the air outlet 66 is shown as being circular. However, other arrangements are envisaged. For example, a rectangular air outlet 66 and associated antibacterial filter could instead be provided. In use, the air outlet 66 of the fluid collection vessel 12 is connected to the air inlet 40 of the pump and control assembly via the aperture 44. In this way, air is pumped out of the fluid collection vessel 12 by the pump 22 so as to subject the fluid collection vessel to vacuum.

A sachet of desiccant (not shown) is placed in the fluid collection vessel 12 during manufacture to increase the viscosity of the collected fluid and thereby reduce sloshing of collected fluid in the fluid collection vessel 12 in use.

The sensor 64 of the fluid collection vessel 12 is used to determine when the fluid collection vessel 12 is substantially full of collected fluid. When undergoing filling, potentially over a period of several days, it is important that the collected fluid in the fluid collection vessel 12 does not contact the sensor 64 prematurely. Thus, the fluid collection vessel has discrete chambers 70, 72 and 74 separated by a system of baffles 76 to minimise the risk of premature sensor contact. This aspect of the fluid collection vessel 12 will now be described in more detail with reference to FIG. 5 which shows a vertical cross-section through the fluid collection vessel 12. It should be noted that, by increasing the viscosity of the collected fluid, the sachet of desiccant further reduces the risk of the collected fluid contacting the sensor 64 prematurely. The fluid collection vessel 12 has a preferred vertical orientation in use, as shown by arrow Z in FIG. 5. In this preferred vertical orientation, the fluid inlet 52 is located at a top corner 68 of the fluid collection vessel 12. In this embodiment, the sensor 64 is arranged to sense when the fluid collection vessel 12 is substantially full even when the fluid collection vessel 12 is tilted by up to about 60 degrees from this preferred vertical orientation. In fact, the maximum tilt angle of the fluid collection vessel in this embodiment is 63 degrees for the sensor 64 to still accurately sense when the fluid collection vessel is substantially full. The location of the sensor 64 on the rear of the fluid collection vessel 12 is shown by dashed lines 64a in FIG. 5.

The fluid collection vessel 12 comprises a number of internal chambers: a main chamber 70, a fluid transfer chamber 72, and a sensor chamber 74 delimited by the system of baffles 76.

The main chamber 70 is the largest chamber and takes up the majority of volume of the fluid collection vessel 12. The window 56 allows viewing of the main chamber 70, and the apertures 58 and 60 pass through the main chamber 70 in this embodiment. A portion of the main chamber 70 is located directly below the fluid inlet 52 when the fluid collection vessel 12 is in its preferred vertical orientation. Similarly, a portion of the main chamber 70 is located directly below the fluid inlet 52 when the fluid collection vessel 12 is tilted by up to 63 degrees in any direction from its preferred vertical orientation. An imaginary cone C is shown by dashed lines in FIG. 5 extending downwardly and outwardly from the fluid inlet 52 at an angle of 63 degrees from the vertical. Any of the fluid collection vessel 12 which falls inside this imaginary cone C is part of the main chamber 70.

The main chamber 70 further comprises a main chamber fluid outlet 77 which leads into the fluid transfer chamber 72. The fluid outlet 77 is located at the top of the fluid collection vessel 12 close to the fluid inlet 52 and outside the imaginary cone C. The fluid outlet 77 is formed by the opening between an end 78 of a baffle 76a and the nearest point 80 on the top of the fluid collection vessel 12. As shown in FIG. 5, the angle between the fluid inlet 52 and the end 78 of the baffle 76a is 63 degrees.

In this embodiment, the fluid outlet 77 only extends along about a third of the depth of the fluid collection vessel 12 in the direction coming out of the page in FIG. 5. This provides further protection against the collected fluid leaving the main chamber 70 until the main chamber 70 is completely full. In this example, the fluid outlet 77 is located near the flat rear half 50a. Thus, FIG. 5 shows a section through the fluid collection vessel 12 close to the flat rear half 50a.

The fluid transfer chamber 72 runs along the central top portion of the fluid collection vessel 12. The baffle 76a separates the fluid transfer chamber 72 from the main chamber 70.

The fluid transfer chamber 72 comprises a fluid outlet 82 which leads into the sensor chamber 74.

The sensor chamber 74 houses the sensor 64 and the air outlet 66. The baffle 76b separates the sensor chamber 74 from the main chamber 70. In this embodiment, the sensor chamber 74 is substantially U-shaped having first and second limbs 84 and 86 and a joining section 88 extending therebetween. Thus, the fluid outlet 82 of the fluid transfer chamber 72 leads into the first limb 84 of the sensor chamber 74. The sensor 64 and the air outlet 66 are located in the second limb 86.

The U-shape of the sensor chamber 74 is vertically oriented when the fluid collection vessel 12 is in its preferred vertical orientation. Thus, the first and second limbs 84 and 86 and the baffles 76b and 76c are vertical in this embodiment. Because the U-shaped sensor chamber 74 is substantially vertical, collected fluid must go down the first limb 84 into the joining portion 88 and then up into the second limb 86 in order to reach the sensor 64.

The air outlet 66 is located nearer the top of the sensor chamber 74 than the sensor 64 is. Thus, the level of collected fluid reaches the sensor 64 before it reaches the air outlet 66 when the fluid collection vessel 12 is in its preferred vertical orientation.

The sensor 64 comprises two spaced electrical contacts within the second limb 86 of the sensor chamber of the fluid collection vessel 12 arranged such that when the level of the collected fluid reaches the sensor location 64a, the collected fluid completes an electrical circuit between the two spaced contacts. In a preferred embodiment, the two spaced electrical contacts are pins protruding into the rear of the fluid collection vessel 12 and spaced apart by a small distance within the sensor location 64a in FIG. 5.

The sensor 64 is also arranged to detect that the fluid collection vessel 12 is correctly fitted to the pump and control assembly 14. Therefore, the sensor 64 comprises a further electrical contact which is arranged to form a complete circuit when the fluid collection vessel 12 is locked into place next to the pump and control assembly 14 by means of the location pegs 62 and sockets 46 as well as the quarter turn lock 48 and apertures 58 and 60. In particular, the further electrical contact is U-shaped and is made up of two pins joined by a bend. The two pins of the U-shaped electrical contact protrude from the rear of the fluid collection vessel 12, and the bend of the U-shaped electrical contact is located within the fluid collection vessel. The two pins of the U-shaped electrical contact are arranged to complete an open electrical circuit in the pump and control assembly 14 when the fluid collection vessel 12 is locked into place as described above.

In use, one end of the tube 16 is inserted into a gauze or other permeable material which is placed within the wound at the fluid collection site. A protective dressing sheet is then affixed over the gauze and the wound. The other end of the tube 16 is connected to the inlet 52 of the fluid collection vessel 12. The pump 22 is then switched on to subject the fluid collection vessel 12 to negative pressure by sucking air out of the air outlet 66 of the fluid collection vessel 12. Thus, a negative pressure gradient is created between the fluid collection site and the fluid collection vessel 12. In this way, fluid is moved from the collection site into the main chamber 70 of the fluid collection vessel 12 via the tube 16.

Because of the arrangement of the chambers 70, 72 and 74 and the baffles 76 therebetween, the main chamber 70 of the fluid collection vessel 12 fills up with collected fluid first, even if the fluid collection vessel 12 is tilted at an angle of up to 63 degrees from its preferred vertical orientation. Once the main chamber 70 of the fluid collection vessel 12 is full of collected fluid, any further collected fluid will overflow from the main chamber 70 firstly into the fluid transfer chamber 72 via the fluid outlet 77 and then into the sensor chamber 74 via the fluid outlet 82. Thus, when fluid reaches the sensor 64 in the sensor chamber 74, the main chamber 70 is already full of collected fluid. In other words, only overflow fluid from the main chamber 70 enters the sensor chamber 74.

Eventually, when the fluid collection vessel 12 is substantially full, the collected fluid will reach a predetermined level as defined by the location 64a of the sensor 64. The fluid will then complete an electrical circuit between the two spaced electrical contacts of the sensor 64 so that the sensor 64 senses that the fluid collection vessel 12 is substantially full. By completion of this electrical circuit, the sensor 64 automatically turns off the pump 22 when the fluid collection vessel 12 is substantially full.

A user is advised that the fluid collection vessel 12 is substantially full via the LCD display of the control panel 20. The user then knows to replace the substantially full fluid collection vessel 12. This is done by disconnecting the tube 16 from the fluid inlet 52 and disconnecting the fluid collection vessel 12 from the pump and control apparatus 14 so that the substantially full fluid collection vessel 12 may be disposed of. A replacement fluid collection vessel (i.e. one that is not substantially full) is then used in place of the old one so as to continue the collection of fluid.

Figure 7:
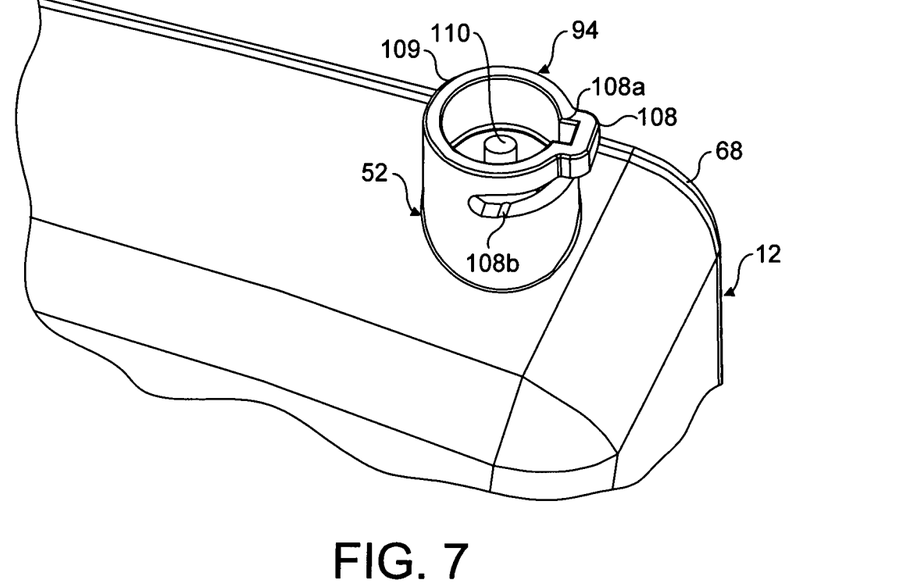
FIG. 7 is a perspective view of the second connector portion shown in FIG. 6b when attached to part of the fluid collection vessel shown in FIGS. 4a and 4b.
Figure 8:
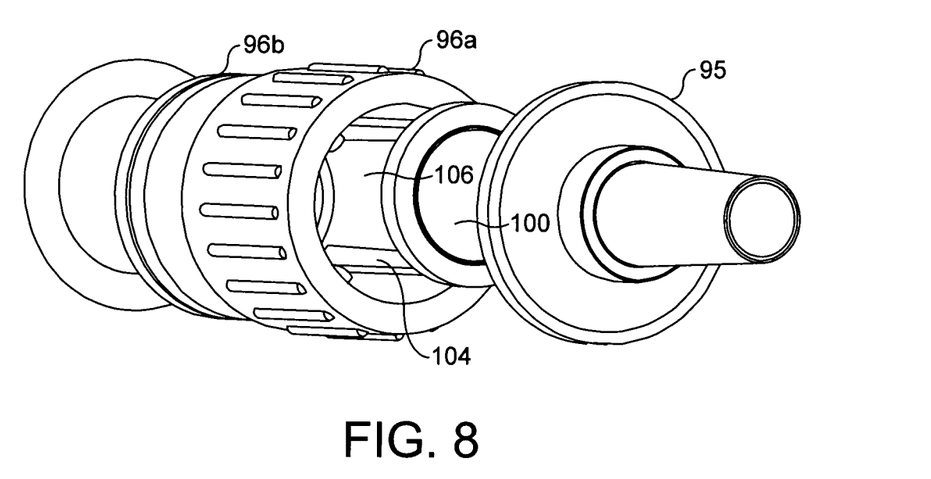
FIG. 8 is an exploded perspective view of the first and second connector portions shown in FIGS. 6a and 6b.

Turning to FIGS. 6a and 6b, these show a preferred embodiment of the connection between the tube 16 and the fluid inlet 52 in much more detail. In addition, perspective views are shown in FIGS. 7 and 8.

FIG. 6a shows a first connector portion 90 coupled to an end 92 of the tube 16. FIG. 6b shows a second connector portion 94 coupled to the fluid inlet 52 of the fluid collection vessel 12. In use, the first and second connector portions 90 and 94 are moveable from a mutually connected configuration to a mutually disconnected configuration. In the connected configuration, the tube 16 is in fluid communication with the fluid collection vessel 12. Whereas, in the disconnected configuration shown in FIGS. 6a and 6b, the first connector portion 90 blocks the flow of fluid through the first connector portion 90 and out of the end 90 of the tube 16.

As shown in FIG. 6a, the first connector portion 90 comprises a protruding bayonet connector 93, a tube connector 95, a conduit 96 formed by a substantially tubular member 97, an O-ring, a disc valve 100, and a spring 102. The tube connector 95 is affixed to the substantially tubular member 97. The O-ring creates a watertight seal with the second connector portion 94 when connected. The disc valve 100 is located within the conduit 96 and is moveable longitudinally along the conduit 96 from a blocking configuration in which the disc valve 100 blocks the passage of fluid through the conduit 96 (as shown in FIG. 6a) to an open configuration in which fluid is able to flow freely through the conduit 96. The spring 100 is a compression spring oriented longitudinally within the conduit 96 so as to bias the disc valve 100 towards the blocking configuration shown in FIG. 6a.

The conduit 96 extends between the end 92 of the tube 16 and the free end 98 of the first connector portion 90. The conduit 96 is substantially tubular. The conduit 96 includes first and second conduit sections 96a and 96b arranged end to end. The first conduit section 96a is a relatively wide conduit such that, if the disc valve 100 is located in the first conduit section 96a, fluid is able to freely flow around the disc valve 100 and through the first conduit section 96a. The second conduit section 96b is a relatively narrow conduit such that, if the disc valve 100 is located in the second conduit section 96b, the disc valve 100 forms a watertight seal within the second conduit section 96b so as to prevent the passage of fluid therethrough. Thus, the internal cross-section of the wide conduit 96a is larger that the internal cross-section of the narrow conduit 96b.

In FIG. 6a, the narrow conduit 96b has a circular cross-section with a diameter equal to the diameter of the disc valve 100. The wide conduit 96a has a circular cross-section with a diameter larger than the diameter of the disc valve 100. It will be appreciated that other valve barrier shapes and other conduit shapes may be used instead of the disc-shaped valve barrier 100 and tubular conduit 96 shown in FIG. 6a.

As is most clearly seen in the exploded perspective view of FIG. 8, there are four longitudinal guiding bars 104 around the edge of the wide conduit 96a. When the disc valve 100 is within the wide conduit 96a, the bars 104 prevent lateral movement of the disc valve 100. Furthermore, when the disc valve 100 is within the wide conduit 96a, fluid can flow around the disc valve 100 along longitudinal slots 106 formed between the bars 104.

As shown in FIGS. 6b and 7, the second connector portion 94 is substantially tubular and comprises a fixed post 110 and a free end 109 having a bayonet receptacle 108.

The bayonet receptacle 108 comprises first and second slots 108a and 108b. The first slot 108a is longitudinally oriented along the longitudinal axis of the substantially tubular second connector portion 94. The second slot 108b is circumferentially oriented around a circumference of the substantially tubular second connector portion 94. In use, the first and second connector portions 90 and 94 are connected together by pushing the free end 98 of the first connector portion 90 into the free end 109 of the second connector portion 94. This engagement can only be accomplished when the protruding bayonet connector 93 is aligned with the first slot 108a. As the first and second connector portions 90 and 94 are connected in this way, the post 110 initially engages a surface of the disc valve 100 and then moves the disc valve 100 from the narrow conduit 96b to the wide conduit 96a. Thus, the engagement of the post 110 with the disc valve 100 during connection of the first and second connector portions 90 and 94 moves the disc valve 100 from the blocking configuration to the open configuration.

Once the protruding bayonet connector 93 has been fully inserted into the first slot 108a, the first connector portion 90 is locked in place by turning the first connector portion 90 relative to the second connector portion 94 so that the protruding bayonet connector 93 moves along the second slot 108b. This turning action does not affect the open configuration disc valve 100.

During subsequent disconnection of the first and second connector portions 90 and 94, the disc valve 100 is no longer being pushed by the post 110. Therefore, due to its biasing, the spring 102 moves the disc valve 100 back from the wide conduit 96a to the narrow conduit 96b, thereby moving it from the open configuration to the blocking configuration. Thus, the first connector portion 90 is drip resistant, i.e. it prevents the risk of fluid dripping from the end of the tube 16 when it is disconnected from the fluid collection vessel 12.

The presence of the bayonet connection (i.e. the protruding bayonet connector 93 and the bayonet receptacle 108) has three purposes. Firstly, the two-step push and turn bayonet connection makes it clear to a user when the first and second connector portions 90 and 94 are properly connected. Secondly, the bayonet connection between the first and second connector portions 90 and 94 is a safety feature to ensure that only appropriate fluid collection tubes 16 are used rather than alternatives which may not be fit for purpose. Thirdly, the bayonet connection is simple to use which is advantageous since it is often necessary to change to the tube 16 before the fluid collection vessel 12 is full.

Although preferred embodiments of the invention have been described, it is to be understood that these are by way of example only and that various modifications may be contemplated.

For example, in an alternative embodiment, it is envisaged that the pump 22 be connected via its air outlet 24 and be arranged to provide positive pressure at the fluid collection site, rather than negative pressure in the fluid collection vessel 12. Thus, the pressure gradient between the fluid collection site and the fluid collection vessel is again negative in this embodiment, thereby acting to move fluid from the fluid collection site into the fluid collection vessel 12 via the tube 16. In this embodiment, the air outlet 66 of the fluid collection vessel is not connected to the pump 22.

Furthermore, it will be appreciated by those skilled in the art that an alternative medical apparatus which only senses substantial fullness of a fluid collection vessel for tilt angles of up to 30 degree or 45 degrees, say, rather than 63 degrees, is also envisaged within the scope of the present invention.

In a further alternative embodiment, a different form of connector could be used from that shown in FIGS. 6a, 6b, 7 and 8. For example, it is possible to use a simple bayonet or screw connector with no automatic shut-off in the disconnected configuration. In this embodiment, no barrier/disc or biasing means/spring need be provided. Instead, the flow could be stopped manually at the appropriate time by means of a pinch clamp on the drain tube 16.

The invention claimed is:

1. A medical apparatus for collecting fluid which has been pumped along a fluid collection conduit from a fluid collection site, the apparatus comprising a fluid collection vessel having a predefined orientation in use, the fluid collection vessel comprising:
   a front wall and a back wall that extend between a top end wall and an opposing bottom end wall;
   a fluid inlet for receiving fluid, wherein in the predefined orientation in use the fluid inlet is located on the top end wall of the fluid collection vessel;
   a sensor chamber;
   an air outlet communicating with the sensor chamber;
   a sensor located in the sensor chamber and arranged to sense when the fluid collection vessel is substantially full even when the fluid collection vessel is tilted by up to a predetermined angle from its predefined orientation; and
   a main chamber defined at its top by a sloping baffle and in fluid communication with the sensor chamber, wherein the main chamber comprises a fluid outlet into the sensor chamber, the main chamber fluid outlet being located at or adjacent to the top end wall of the fluid collection vessel and outside an imaginary cone which, when the fluid collection vessel is in its predefined orientation, extends downwardly and outwardly from the fluid inlet at the predetermined angle, and wherein the angle between the fluid inlet and the top most end of the sloping baffle defines the imaginary cone such that fluid entering the fluid collection vessel via the fluid inlet flows into the main chamber even when the fluid collection vessel is tilted by up to the predetermined angle from its predefined orientation, and, once the main chamber is full, any further collected fluid flows from the main chamber in to the sensor chamber, at least a portion of the main chamber extending between the top end wall and the bottom end wall;

wherein the sensor chamber comprises a substantially U-shaped chamber having first and second limbs and a joining section extending therebetween, the first and second limbs being substantially vertically oriented when the fluid collection vessel is in the predefined orientation in use, the first limb of the substantially U-shaped chamber being in fluid communication with the main chamber, the sensor being disposed in the second limb of the substantially U-shaped chamber, the substantially U-shaped chamber extending between the top end wall and the bottom end wall so as to have a height substantially equal to the height of the main chamber.

2. The medical apparatus of claim 1 wherein the predetermined angle is 30 degrees.

3. The medical apparatus of claim 1 wherein the predetermined angle is at least 45 degrees.

4. The medical apparatus of claim 1 wherein the predetermined angle is at least 60 degrees.

5. The medical apparatus of claim 1 wherein the fluid collection vessel comprises one or more baffles to restrict the direct flow of fluid from the main chamber towards the sensor.

6. The medical apparatus of claim 1 wherein the fluid collection vessel further comprises a fluid transfer chamber in fluid communication between the main chamber fluid outlet and a fluid inlet of the sensor chamber.

7. The medical apparatus of claim 1 wherein the sensor triggers when immersed in fluid.

8. The medical apparatus of claim 7 wherein the sensor comprises two spaced electrical contacts within the fluid collection vessel arranged such that when the fluid collection vessel is substantially full, the fluid completes an electrical circuit between the two spaced contacts.

9. The medical apparatus of claim 1 wherein the fluid collection vessel is disposable.

10. The medical apparatus of claim 1 wherein the air outlet is located close to the sensor.

11. The medical apparatus of claim 1 further comprising a fluid collection conduit for conveying fluid from the fluid collection site to the fluid inlet of the fluid collection vessel.

12. The medical apparatus of claim 11 further comprising a pump operable to pump fluid along the fluid collection conduit from the fluid collection site to the fluid collection vessel, wherein the pump is operable to apply negative pressure within the fluid collection vessel so as to pump fluid along the fluid collection conduit from the fluid collection site to the fluid collection vessel.

13. The medical apparatus of claim 11 further comprising a pump operable to pump fluid along the fluid collection conduit from the fluid collection site to the fluid collection vessel, wherein the pump is operable to apply positive pressure at the fluid collection site so as to pump fluid along the fluid collection conduit from the fluid collection site to the fluid collection vessel.

14. The medical apparatus of claim 1 further comprising a pump operable to pump fluid along the fluid collection conduit from the fluid collection site to the fluid collection vessel.

15. The medical apparatus of claim 14, wherein the sensor is arranged to automatically turn off the pump when the sensor senses that the fluid collection vessel is substantially full.

16. The medical apparatus of claim 1, wherein at least one of the first and second limbs of the sensor chamber extends linearly between the joining section and the top end wall.

17. The medical apparatus of claim 1, wherein the first and second limbs of the sensor chamber are disposed in substantially parallel alignment between the joining section and the top end wall.

18. The medical apparatus of claim 1, wherein a second baffle separates the first and second limbs of the sensor chamber, the second baffle linearly projecting from the top end wall toward the bottom end wall.

19. The medical apparatus of claim 1, wherein when the fluid collection vessel is in the predefined orientation, the slopping baffle slopes continuously downward from a first end disposed toward the air inlet to an opposing second end, the second end connecting to a third baffle that extends to the bottom end wall, the third baffle bounding one side of the first limb of the sensor chamber.

* * * * *